United States Patent [19]

Domb et al.

[11] Patent Number: 4,857,311

[45] Date of Patent: * Aug. 15, 1989

[54] POLYANHYDRIDES WITH IMPROVED HYDROLYTIC DEGRADATION PROPERTIES

[75] Inventors: Abraham J. Domb, Brookline; Robert S. Langer, Somerville, both of Mass.

[73] Assignee: Massachusetts Institute of Technology, Cambridge, Mass.

[*] Notice: The portion of the term of this patent subsequent to Jul. 12, 2005 has been disclaimed.

[21] Appl. No.: 80,631

[22] Filed: Jul. 31, 1987

[51] Int. Cl.[4] .................... A61K 31/74; C08G 63/00
[52] U.S. Cl. ...................................... 424/78; 528/271
[58] Field of Search ........................ 424/78; 528/271

[56] References Cited

U.S. PATENT DOCUMENTS 2,071,250  2/1937  Carother .............................. 528/230

OTHER PUBLICATIONS

K. W. Leong et al., 1985, J. of Biomed. Materials, vol. 19, 941–955.
Encyclopedia of Polymer Sci. & Tech., vol. 10 (1969), pp. 630–653.
Leong, et al., J. Biomed., Mater. Res. 20, 51 (1986).
Hill, *J.A.C.S.*, 52, 4110, (1930).
Hill, *J.A.C.S.*, 54, 1569, (1932).
Rosen, et al., *Biomaterials* 4, 131 (1983).
Leong, et al., *Macromolecules* 20(4), 705–712, (Apr. 1987).

Primary Examiner—Joseph L. Schoffer
Assistant Examiner—Peter F. Kulkosky
Attorney, Agent, or Firm—Kilpatrick & Cody

[57] ABSTRACT

Polyanhydrides with uniform distribution of alkyl and aromatic residues are prepared by melt polycondensation or solution polymerization of p-carboxyphenoxyalkanoic acids or p-carboxyphenylalkanoic acids. These polymers are soluble in common organic solvents and have low melting points, generally in the range of 40°–100° C.

The polyanhydrides are especially well suited for forming bioerodible matrices in controlled bioactive compound delivery devices. A polymeric matrix formed according to the method described here degrades uniformly during drug release, preventing the wholescale channeling of the bioactive compound into the environment, and eliminating the problem of the presence of the polymer matrix at the site long after drug release. The polymer displays zero-order kinetic degradation profiles over various periods of time (days to months), at a rate useful for controlled drug delivery. Furthermore, a desired degradation rate may be obtained by choosing the appropriate length of the aliphatic moiety.

18 Claims, 3 Drawing Sheets

□ PCPA (x=1)
♦ PCPV (x=4)
■ PCPO (x=7)

POLYANHYDRIDES WITH IMPROVED HYDROLYTIC DEGRADATION PROPERTIES

BACKGROUND OF THE INVENTION

This invention is in the area of organic synthetic chemistry and is in particular a method of preparing a polyanhydride polymer which contains a uniform distribution of aliphatic and aromatic residues for use as a bioerodible matrix material for controlled bioactive compound delivery systems.

Biodegradable controlled release systems for bioactive compounds have an advantage over the other controlled release systems in obviating the need to surgically remove the drug depleted device. The device is implanted under the skin, and degrades during bioactive compound release. Drug loaded devices are generally fabricated by solvent casting, injection molding or compression molding. Injection molding is conducted at temperatures above the melting point of the polymer, and so it is important to construct a polymer which has a melting point lower than the temperature at which drugs begin to degrade or react with the matrix.

Properties of the polymer matrix material other than melting point are very important to obtaining the proper release of the drug. To be useful as a matrix for controlled release of a biologically active substance, the polymer composition must undergo surface erosion in the in vivo environment, rather than bulk erosion. Surface erosion occurs when the rate of hydrolytic degradation on the surface is much faster than the rate of water penetration into the bulk of the matrix. This deters whole scale permeation of the drug molecules into the environment. Bulk erosion occurs when the polymers incorporate water in the center of the matrix, rendering the entire polymer composition sponge like. This results in the break up of the matrix, and creates a channeling effect in which the bioactive compound is released from the matrix. Bulk erosion is directly related to the sensitivity of the polymer composition to hydrolysis. The matrix degrades heterogeneously when it erodes from the surface, and homogeneously when it erodes evenly from the surface and the interior. Polymers which undergo bulk erosion (homogeneous degradation) include polylactic acid, polyglutamic acid, polycaprolactone and lactic/glycolic acid copolymers.

The ideal polymer must have a hydrophobic backbone, but with a water labile linkage. Many classes of polymers, including polyesters, polyamides, polyurethanes, polyorthoesters, polyacrylonitriles, and polyphosphazenes, have been studied for controlled delivery applications, but few, except for polyorthoesters, have been designed with these considerations in mind. Leong, K. W., Brott, B. C. and Langer, R., *J. Biomed. Mater. Res.* 19, 941, 942 (1985). Polyorthoesters, furthermore, erode from the surface only if additives are included in the matrix. Taking advantage of the pH dependence of the rate of orthoester cleavage, preferential hydrolysis at the surface is obtained by either addition of basic substances to suppress degradation in the bulk, or incorporation of acidic catalysts to promote degradation on the surface. Polyanhydrides are well suited as a biodegradable system because they erode in a heterogeneous manner without requiring any such additives.

The degradation products of polyanhydrides are nonmutagenic, noncytotoxic and have a low teratogenic potential, Leong, K. W., D'Amore, P. D., Marletta, M., and Langer, R., *J. Biomed. Mater. Res.* 20, 51 (1986), which further confirms the utility of these compound for in vivo use.

Polyanhydrides were initially proposed by Hill and Carothers in the 1930s to be a substitute for polyesters in textile applications. Hill, J. *J.A.C.S.* 52, 4110 (1930); Hill, J.; and Carothors, W. H. *J.A.C.S.* 54, 1569 (1932). The idea was later rejected because of their hydrolytic instability. It is this property, however, that renders polyanhydrides appealing for controlled release applications. The hydrophilic anhydride linkage ensures biodegradability and may be synthesized with a variety of backbones. It was earlier shown that a model polyanhydride, poly[bis(p-carboxyphenoxy) methane anhydride], displayed near zero-order erosion and release kinetics at 37° and 60° C. Rosen, H. B.; Chang, J.; Wnek, G. E.; Linhardt, R. J.; Langer, R., Bioerodible polyanhydrides for controlled drug delivery, *Biomaterials* 4, 131 (1983).

Later, three other related compounds, poly 1,3-[bis(p-carboxyphenoxy)propane anhydride] (p(CPP)), the polymer formed from copolymerization 1,3-bis(p-carboxyphenoxy)propane with sebacic acid (p(CPP-SA)), and polyterephthalic acid anyhydride were synthesized and tested for their drug matrix properties. Leong, K. W.; Brott, B. C.; Langer, R., Bioerodible polyanhydrides as drug carrier matrices; *J. Biomed. Mater. Res.* 19, 941 (1985). The hydrophobic polymers of p(CPP) and p(CPP-SA) (in a 85:15 ratio) displayed constant erosion kinetics over several months, and by extrapolation it was estimated that p(CPP) would completely degrade in over three years. Degradation rates in the range of $10^{-1}$ to $10^{-4}$ mg/h/cm2 were obtained.

Degradation rates were increased significantly by the addition of a compound with more labile anhydride linkages, such as sebacic acid. The compounds which hydrolyze more easily, however, tend to have channeling problems at a stage of about 60% degradation.

Channeling occurs when sufficient anhydride bonds are cleaved in the same region of the matrix that wholescale permeation of the bioactive compound into the environment occurs. For example, in the CPP-SA copolymer, the aliphatic anhydride bonds are cleaved and all drug is released in 10 days (60% degradation), yet the aromatic anhydride regions of the matrix remain for another 5½ months. See FIG. 1.

The problem that has arisen to date with the use of polyanhydride copolymers as a biodegradable matrix is that if the matrix is very sensitive to hydrolysis, the device absorbs water promoting degradation in the interior of the matrix (homogeneous degradation), which results in a channeling effect. Aliphatic anhydrides in these polymer compositions are more sensitive to hydrolysis than aromatic anhydrides. When aromatic and aliphatic diacids are randomly copolymerized, a non uniform chain structure is obtained which contains regions of aliphatic character, resulting in non uniform degradation and breakup of the matrix.

The problem of bioactive compound channeling in the past was exacerbated by the low molecular weights of the polymers. In Co-pending patent application Ser. No. 892,809, filed Aug. 1, 1986, entitled "Synthesis and Application of High Molecular Weight Polyanhydrides," by Abraham J. Domb and Robert S. Langer, high molecular weight polyanhydrides were formed by melt polycondensation of highly pure isolated prepolymers under optimized reaction conditions, with the optimal inclusion of a catalyst. These higher molecular weight polyanhydrides have improved physico-mechanical properties, however, regions of aliphatic anhydride still present problems of premature release of the drug.

If the polyanhydride is aromatic, although a zero order hydrolytic degradation profile is displayed, the rate of degradation is so slow that the compounds are limited to long-term applications (years). Furthermore, they cannot be fabricated into microspheres or films from solutions because they have low solubility in common organic solvents and have high melting points, which results in the destruction of the drug on preparation of the controlled release device.

It is therefore an object of this invention to provide a method of preparing a polyanhydride polymer composition which degrades uniformly over time in an aqueous medium, and at a rate useful for controlled bioactive compound delivery.

It is another object of this invention to provide a method of preparing a polymer which is soluble in organic solvents and has a low melting point, generally in the range of 40°–100° C., in order to be able to fabricate the controlled release drug device into microspheres or films from solution, or to prepare such compositions by injection molding.

SUMMARY OF THE INVENTION

The present invention is a method of preparing polyanhydrides with a uniform distribution of aliphatic and aromatic residues in the chain, which property imparts valuable characteristics to the polymer for use as a bioerodible matrix material in controlled bioactive compound delivery devices.

In the preferred mode, the polyanhydrides are synthesized by melt polycondensation or solution polymerization of p-carboxyphenoxyalkanoic acids, as defined by the formula

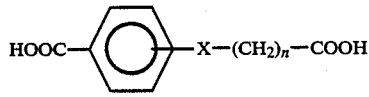

wherein $n=2$ to 25 and $X=O$ or p-carboxyphenylalkanoic acids, ($X=CH_2$, $n=2$ to 25).

Because of the fine distribution of aliphatic and aromatic groups in the polymer matrix, the matrix degrades uniformly. Aliphatic anhydrides hydrolyze more rapidly than aromatic anhydrides. However, because there are no more than two aliphatic moieties linked together, the aliphatic hydrolysis results in many fine breaks (or pores) in the matrix, limiting bioactive compound release during the later period in which the aromatic anhydride bonds are being cleaved. Hydrolytic degradation of these polyanhydrides display zero-order kinetics, indicative of surface erosion of the matrix. Integrity of the matrix is maintained during hydrolysis, as indicated by the fact that drug release rates closely follow polymer degradation rates. The matrix does not degrade homogeneously before 60% heterogeneous degradation, and more usually, not until greater than 90% heterogeneous degradation has taken place.

Furthermore, degradation rates are accomplished which typify the time frames needed for drug release (days-months). The rate of degradation is dependent on the length of the aliphatic residue in the monomer unit. As an example, poly (p-carboxyphenoxyvaleric anhydride), with four alkyl carbons per monomer, completely degrades in less than 20 days, whereas poly (p-carboxyphenoxyoctanoic anhydride), with seven alkyl carbons, degrades in less than 120 days.

The utility of these polyanhydrides for bioerodible matrix materials is further demonstrated by their low melting points (in the range of 40°–100° C.), and their solubility in organic solvents.

DETAILED DESCRIPTION OF THE INVENTION

Figure 1:
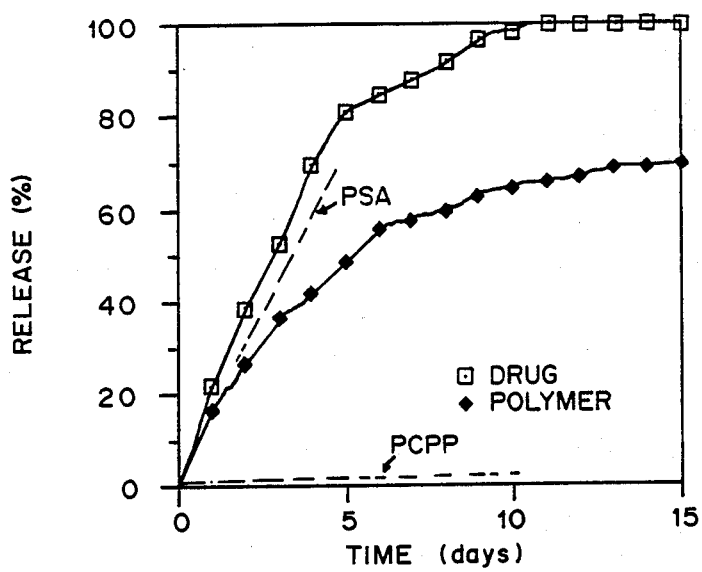
FIG. 1. is a graph of the release of model drug (p-nitroaniline from the matrix material comprised of p(CPP-SA)(1:1) versus time, along with the percentage degradation of the matrix material itself over time.

The present invention is a method for synthesizing polyanhydride polymers which have a uniform distribution of aliphatic and aromatic residues, are soluble in organic solvents, have low melting points (in the range of 40°–100° C.) and which hydrolytically degrade in periods of days to months without undergoing bulk erosion. These properties are essential to a useful bioerodible matrix material for controlled drug delivery devices.

The method for preparing such polyanhydride polymers consists of choosing a monomer of the general chemical structure

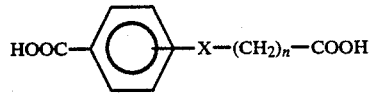

where $X=O$ or $CH_2$, and $n=$an integer between 2 and 25.

When such monomers are polymerized according to the methods described below, namely by melt polycondensation of prepolymers or solution polymerization, polymers result which contain a uniform distribution of aliphatic and aromatic groups. The aliphatic-aromatic diacids are connected by an anhydride bond

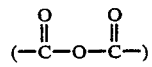

in the polymer. Since the monomer has a "head," the aromatic region, and a "tail," the aliphatic region, these monomers connect to form the polymer in three ways: tail to tail, head to head, and head to tail (or tail to head). Because of this, the largest aliphatic chain between two aromatic residues in the polymer consists of two units, which occurs when the the polymer in three ways: tail to tail, head to head, and head to tail (or tail to head). Because of this, the largest aliphatic chain between two aromatic residues in the polymer consists of two units, which occurs when the anhydride results from a "tail to tail" reaction between monomer units. This controls the problem found with the use of copolyanhydrides to date as a controlled drug delivery device; the wholesale channeling of bioactive compound from the matrix due to bulk erosion caused by regions of aliphatic moieties which are more sensitive to hydrolysis.

The polymeric matrix degrades hydrolytically in a two phase process. Since aliphatic anhydrides hydrolyze faster than aromatic anhydrides, the first phase consists of the cleavage of the aliphatic bonds. Because there are no more than two aliphatic moieties linked together, the aliphatic hydrolysis result in many fine breaks (or pores) in the matrix. The integrity of the matrix is maintained, and the device continues to limit bioactive compound release. In the second phase, the aromatic anhydrides are hydrolyzed, resulting in the degradation of the matrix.

The method of the present invention also consists of choosing monomers which will polymerize into polyanhydrides with low melting points (within the range of 40°–100° C.) and which are soluble in organic solvents. This solves the problem to date of the inability to fabricate long acting polymers into microspheres or films because of low solubility and high melting point of the product.

By this method of preparing a polymer with uniform aliphatic and aromatic regions, a rate of degradation is obtained which is better suited to controlled release delivery devices than the rates obtained by the use of compounds less sensitive to hydrolysis, such as aromatic polymers.

As stated above, these polyanhydride compositions are valuable as controlled bioactive compound delivery devices. A bioactive compound is any compound which has a direct or indirect biological effect. Examples are drugs, proteins, hormones, antibodies, nucleic acids and saccharides. The bioactive compound is embedded into the polymer and then implanted or controlled delivery, in vivo.

I. Synthesis of the monomers

The following provides the preferred method of synthesis of these uniform aliphatic-aromatic polymers.

Infared spectroscopy of the monomers and polymers was performed on a Perkin-Elmer 1430 spectrophotometer. Polymeric samples were film cast onto NaCl plates from a solution of the polymer in chloroform. Monomer and prepolymer samples were either pressed into KBr pellets or dispersed in nujol onto NaCl plates.

The melting points of prepolymers were determined on a Fisher Johns melting point apparatus.

The molecular weights of the polymers and prepolymers were estimated on a Perkin-Elmer GPC system consisting of the series 10 pump and the 3600 Data Station with The LKB 214-rapid spectral detector at 254 nm wavelength. Samples were eluted in chloroform through two PL Gel columns (Polymer Laboratories; 100 A and 1000 A pore sizes) in series at a flow rate of 1.5 ml/min. Molecular weights of polymers were determined relative to polystyrene standards (Polysciences; polyanhydrides with molecular weights from 500 to 1,500,000) using CHROM 2 and GPC 4 computer programs (Perkin-Elmer, Mass.).

$^1$H-NMR spectra were obtained on a Varian 250 MHz spectrophotometer, using deuterated chloroform as a solvent and tetramethylsilane as an internal reference.

UV measurements were performed on a Perkin-Elmer 553 UV/VIS spectrophotometer.

The methyl p-carboxyphenoxyalkanoate monomers were prepared according to the method of Izard. Izard, C. F.; Kworek, X. I. *J. Am. Chem. Soc.* 1951, 73, 1861, (1951) as follows:

Preparation of P-Carboxyphenoxyalkanoic acids

Freshly cut sodium metal (5.98 g, 0.26 mole) was gradually introduced into 150 ml of dry methanol in a 1000 ml flask equipped with a stirrer, and a reflux condenser with a drying tube. Upon complete solution of the sodium, first, 39.56 g (0.26 mole) of methyl p-hydroxybenzoate in 100 ml of methanol and later 50.0 g (0.26 mole) of methyl 5-bromovalerate were added rapidly. The reaction was allowed to reflux for 78 hours. After 78 hours of refluxing precipitated material was removed by filtration. The diester was precipitated upon pouring the solution into an ice water mixture. A clear powdery white precipitate was obtained, and filtered from the remaining solution. The precipitate was dried overnight, and weighed to obtain 58.35 g (84% yield). Methyl p-carboxyphenoxyacetate (CPA), (85% yield), and methyl p-carboxyphenoxyoctanoate (CPO) (75% yield) were prepared similarly using methyl bromoacetate, and methyl 8-bromooctanoate, respectively. The data analysis of the esters is described in Table 1. The methyl esters were then hydrolyzed to the corresponding diacids as follows:

600 ml of 2 N NaOH solution is added to 58.35 g of methyl p-carboxyphenoxyvalerate in a 1000 ml flask equipped with a condenser and stirrer. The solution is allowed to reflux for 10 hours while stirring. The solution is allowed to cool to room temperature. The compound is then isolated by lowering the pH of the solution from 12 to less than 1 by adding concentrated sulfuric acid. The precipitate is filtered from solution and allowed to dry overnight (57.00 g, 93% yield). CPA and CPO were hydrolyzed to the diacid similarly. The data analysis is described in Table 1.

II. Polymerization of the monomers

These monomers may be polymerized by the method of melt polycondensation of prepolymers or by solution polymerization.

A. The method of melt polycondensation of prepolymers is described in Domb, A. J.; Langer, R., *J. Poly Sci* 1986 (in press). The prepolymers are formed by heating the diacid with acetic anhydride. For example, 600 ml of acetic anhydride is added to 57.0 g of p-carboxyphenoxyvaleric acid (CPV) in a flask equipped with a condenser and a stirrer. The reaction is refluxed for six hours while stirring. The reaction mixture is evaporated to dryness. To the residue is added a 1:1 mixture of ether: petroleum ether to remove excess acetic anhydride. This is allowed to set overnight and then the solvent mixture is decanted. This procedure is repeated with petroleum ether. The prepolymer is then isolated by filtration and dried (50 g., 65% yield). Data analysis of the prepolymers is given in Table 2.

TABLE 1

Data analysis of methyl-(p-carboxyphenoxy)alkanoates and the corresponding diacids

| Products | Mp (°C.) | IR(cm$^{-1}$)[a] | H—NMR (ppm) |
|---|---|---|---|
| CPA diester | 94–95 | 1770, 1710, 1600 | CDCl$_3$, TMS, 0–9 ppm (8.0,d,2H,J = 6Hz),(6.9,d,2H,J = 6Hz), (4.7,s,2H,J = 0Hz),(3.9,s,3H,J = 0Hz), (3.8,s,3H,J = 0Hz). |
| CPV diester | 43–45 | 1740, 1710, 1600 | CDCl$_3$,TMS,0–9 ppm (8.0,d,2H,J = 9Hz),(6.9,d,2H,J = 9Hz), (4.0,t,2H,J = 5Hz),(3.9,s,3H,J = 0Hz), (3.7,s,3H,J = 0Hz),(2.4,t,2H,J = 6Hz), (1.8,quintet,4H,J = 0.5Hz). |
| CPO diester | 57–58 | 1730, 1710, 1600 | CDCl$_3$,TMS, 0–9 ppm (7.8,d,2H,J = 3Hz),(7.0,d,2H,J = 3Hz), (4.0,t,2H,J = 5Hz),(3.9,s,3H,J = 0Hz), (3.6,s,3H,J = 0Hz),(2.2,t,2H,J = 3Hz), (1.7,quintet,2H,J = 5Hz),(1.5,quintet,2H,J = 5Hz) (1.3,s,6H,J = 0Hz). |
| CPA diacid | 158–162 | 1730, 1710, 1600 | D$_2$O + K$_2$CO$_3$,0–9 ppm (7.8,d,2H,J = 4Hz),(6.9,d,2H,J = 4Hz), (4.5,s,2H,J = 0Hz). |
| CPV diacid | 195–198 | 1690, 1600 | D$_2$O + K$_2$CO$_3$, 0–9 ppm (7.8,d,2H,J = 3Hz),(6.9,d,2H,J = 3Hz) (3.9,t,2H,J = 2Hz),(2.2,t,2H,J = 5Hz) (1.7,s,4H,J = 0Hz). |
| CPO diacid | 204–206 | 1690, 1680, 1600 | D$_2$O + K$_2$CO$_3$,0–9 ppm (7.8,d,2H,J = 3Hz),(7.0,d,2H,J = 3Hz), (4.0,t,2H,J = 5Hz),(2.2,t,2H,J = 3Hz), (1.7,quintet,2H,J = 5Hz),(1.5,quintet,2H,J = 5Hz) (1.3,s,6H,J = 0Hz). |

[a]characteristic for ester or acid respectfully.

TABLE 2

Data analysis of p-carboxyphenoxyalkanoic acid prepolymers[a]

| Prepolymers Of: | Melting Point (°C.) | Molecular Weight Mn | Molecular Weight Mw | IR[b] (cm$^{-1}$) |
|---|---|---|---|---|
| Poly (CPA) | 61–62 | 187 | 195 | 1820, 1790, 1730, 1600 |
| Poly (CPV) | 54–55 | 231 | 995 | 1820, 1740, 1600 |
| Poly (CPO) | 59–60 | 418 | 1322 | 1800, 1730, 1600 |

[a]Prepolymers prepared from the reaction with acetic anhydride. Molecular weight was determined by GPC.
[b]Characteristic for anhydride bonds (1720-1820 cm$^{-1}$), and aromatic ring (1600 cm$^{-1}$).

The prepolymers underwent melt-condensation as follows: in a typical reaction, CPV prepolymer (2.0 g) was placed in a glass tube 2×20 cm (Kimax) with a side arm equipped with a capillary nitrogen inlet. The tube was immersed in an oil bath at 180° C. After the prepolymers were melted (1 min), high vacuum (0.1 mm Hg) was applied through the side arm. The condensation product (acetic anhydride) was collected in an acetone/dry ice trap. Polymerization was continued for 90 minutes. The crude polymer was purified by precipitation in dry petroleum ether from a chloroform solution. For melting point, IR spectra analysis and molecular weight see Table 3. Elemental analysis: p(CPA) (C$_9$H$_6$O$_4$) C 59.2, O 35.4, H 3.1 (cal. C 60.7, O 35.9, H 3.4); p(CPV) (C$_{12}$H$_{12}$O$_4$) C 63.7, O 29.5, H 5.1 (cal. C 64.5, O 29.1, H 5.5); p(CPO) (C$_{15}$H$_{18}$O$_4$) C 68.2, O 24.1, H 6.5 (cal. C 68.7, O 24.4, H 6.9).

TABLE 3

Poly (p-carboxyphenoxy) alkanoic anhydride[a]

| Polymer | Molecular Weight Mw | [n] dl/g | Melting Point (°C.) |
|---|---|---|---|
| Poly (CPA) | — | — | 204° C. |
| Poly (CPY) | 44,600 | 0.58 | 50–51 |
| Poly (CPO) | 33,300 | 0.46 | 53–54 |
| Poly (CPV-CPO)(1:1) | 24,600 | 0.37 | 40–45 |

TABLE 3-continued

Poly (p-carboxyphenoxy) alkanoic anhydride[a]

| Polymer | Molecular Weight Mw | [n] dl/g | Melting Point (°C.) |
|---|---|---|---|
| Poly (CPV-CPA)(1:1) | 21,800 | 0.32 | 62–65 |
| Poly (CPC-CPA)(1:1) | 20,855 | 0.31 | 58–60 |

[a]Synthesized by melt polycondensation. Molecular weight was determined by GPC; viscosity was measured in chloroform at 23° C.

B. Solution Polymerization of polyanhydrides was taught by Domb, A. J.; Ron, E., and Langer, R., *Macromolecules* 1987 (submitted for publication); and further described in detail in U.S. Ser. No. 080,332, filed July 31, 1987 by Domb, et al. entitled "One Step Polymerization of Polyanhydrides".

The optimal procedure for solution polymerization of these polyanhydrides is as follows:

Diphosgene (0.5 g, 0.5 eq.) is added dropwise into a stirred mixture of p-carboxyphenoxyvaleric acid (2 g, 1.0 eq.) and poly(4-vinylpyridine) (PVP) (3.0 g, 2.5 eq.) in 20 ml chloroform.

After three hours at 25° C., the insoluble PVP.HCl is removed by filtration. The filtrate is isolated by filtration, washed with anhydrous ethyl ether and dried at 25° C. for 24 hours in a vacuum oven. (In the preferred mode, poly(p-carboxyphenoxy)acetic anhydride is polymerized with the use of triethylamine (TEA)).

Table 4 describes the molecular weight, polymer yield and melting point of several illustrative polyanhydrides with uniform aliphatic and aromatic residues, polymerized in solution. Poly [p-carboxyphenoxyacetic anhydride] has been described in *Ency. of Poly Sci and Tech* (10) 630, 644 (1969).

TABLE 4

Solution polymerization of p-carboxyphenoxy alkanoic acids[a]

| Polymer | Molecular Weight Mw | Mn | Polymer Yield % | Melting Point (°C.) |
|---|---|---|---|---|
| Poly (CPA) | — | — | 77 | 185 |

TABLE 4-continued

Solution polymerization of p-carboxyphenoxy alkanoic acids[a]

| Polymer | Molecular Weight Mw | Mn | Polymer Yield % | Melting Point (°C.) |
|---|---|---|---|---|
| Poly (CPV) | 12850 | 6450 | 68 | 50–52 |
| Poly (CPO) | 9400 | 4490 | 75 | 48–51 |
| Poly (CPV-CPO) | 10250 | 4810 | 72 | 40–42 |
| Poly (CPA-CPV) | 9150 | 4900 | 67 | 55–58 |
| Poly (CPA-CPO) | 11210 | 5010 | 81 | 54–56 |

[a]Polymerized in chloroform at 25° C. using poly (4-vinylpyridine) as acid acceptor and diphosgene as coupling agent. Molecular weight was determined by GPC. (CPA) refers to p-carboxyphenoxyacetic acid, (CPV) referes to p-carboxyphenoxyvaleric acid, (CPO) refers to p-carboxyphenoxyoctanoic acid.

Polymers synthesized according to the method above were characterized by NMR. As stated above, because a monomer is used which has both an aliphatic and an aromatic region, the aliphatic-aromatic diacids can be connected by anhydride bond in the polymer by either: 1. aliphatic moiety and aliphatic moiety ("tail to tail") 2. aliphatic moiety and aromatic moiety ("tail to head" or "head to tail") 3. aromatic moiety and aromatic moiety ("head to head").

These three possibilities are reflected in the IR and $^1$H-NMR spectra. Anhydride carbonyl stretchings at 1720, 1780, and 1800 cm$^{-1}$ characteristic of aliphatic anhydrides (1720, 1800 cm$^{-1}$), and conjugated noncyclic anhydrides (1720, 1780 cm$^{-1}$), are observed, which indicate the existence of all of the possibilities. The distribution of the three types of anhydride bonds in the polymer was determined by NMR. The methylenic protons of the aliphatic residue conjugated to the anhydride bond is split into two triplets, with similar integrations at 2.54 ppm, (J=3 Hz) and 2.72 ppm (J=3 Hz). The aromatic protons (2H ortho to carboxylic acid substituent) are split into two doublets, at 7.99 (J=8 Hz), and 8.1 (J=8 Hz). These splittings do not show in the prepolymers. It is likely that the splitting in the polymer is due to the chemical shift influenced by the other substitute of the anhydride bond. For the aliphatic substituents ("tail to tail") the chemical shift is 2.54 ppm. For the aliphatic - aromatic substituent ("head to tail" or "tail to head") the chemical shift is 2.72. The aromatic hydrogens are interpreted similarly, where aliphatic-aromatic ("head to tail") is at 7.95 ppm and aromatic-aromatic ("head to head") at 8.10 ppm. From the integration results the ratio between the anhydrides is: 2:1:1 "head - tail, "head - head," and "tail - tail" respectively. Identical findings were found for poly(CPO).

The polymers synthesized according to this method are stable when stored at 25° C. under vacuum. Specifically, after six months of storage, p(CPV) and p(CPO) did not show any decrease in molecular weight and are pliable.

II. Melting Point and Solubility in Organic Solvents

The polymers synthesized according to the method herein display low melting points, as indicated in Table 3, and are soluble in organic solvents, such as chloroform, and methylene chloride up to 40% w/v. These properties of the aliphatic-aromatic polymeric anhydrides allow for fabrication into microspheres or films from solution.

III. Hydrolytic Degradation

Figure 2:
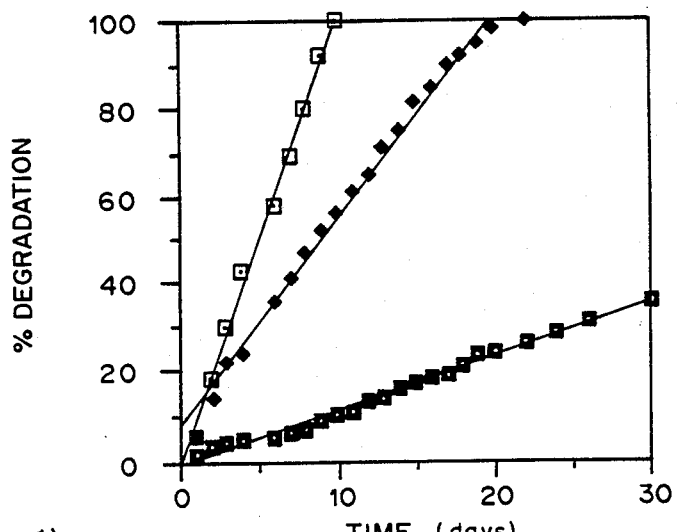
FIG. 2. is a graph of the percentage of hydrolytic degradation of three p-carboxyphenoxyalkanoic polyanhydrides over time in phosphate buffer (0.1 M, pH 7.40) at 37° C.

Hydrolytic degradation of these aliphatic-aromatic polymers display zero-order kinetic degradation profiles. A zero-order kinetic degradation profile results in a linear relationship between percentage degradation and time. At 37° C. in phosphate buffer (0.1 M, pH 7.40), poly(CPA), poly(CPV) and poly (CPO) maintain a linear relationship up to 100% degradation. See FIG. 2. This demonstrates that surface erosion, as opposed to bulk erosion, is taking place.

These compounds further display their integrity over time when degradation rates are measured in conjunction with drug release rates. Drug incorporated matrices were formulated by compression molding. The model drug p-nitro aniline (PNA), sieved to the same size range, was mixed with 200 mg polymer manually and the mixture was pressed onto circular discs of 15 mm diameter and 1 mm thick in a Carver Test Cylinder Outfit at 30 Kpsi. P-Nitroaniline is used as a model drug because it absorbs strongly in the near visible range and provides minimum interference with the UV analysis of the matrix degradation products. The polymer erosion and drug release kinetics were followed by measuring the UV absorbance of the periodically changed buffer solutions in the Perkin-Elmer UV spectrophotometer. The optical densities at 381 nm (absorption maximum for p-nitroaniline) and 250 nm for degradation products were measured to determine the respective results.

Figure 3:
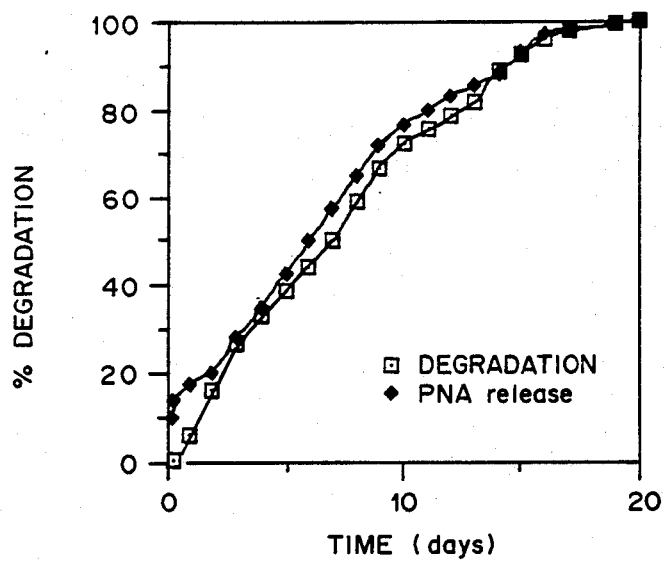
FIG. 3. is a graph of the release of p-nitroaniline (PNA) from the matrix material comprised of poly p-carboxyphenoxyvaleric anhydride [p(CPV)] versus time, along with the percentage degradation of the matrix material itself [p(CPV)] over time.
Figure 4:
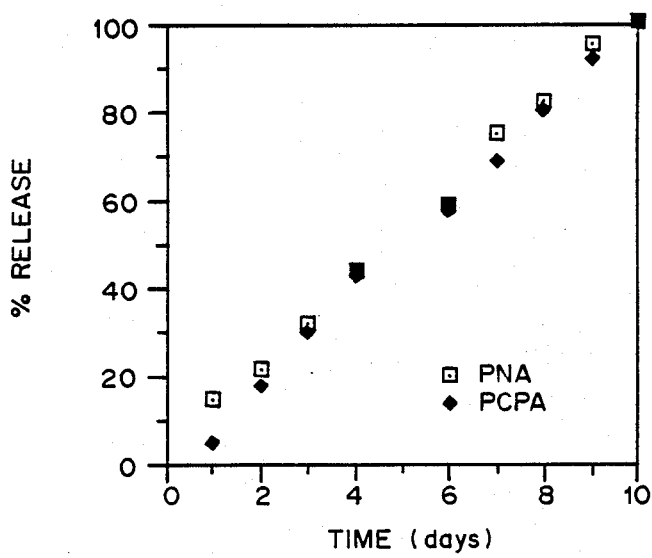
FIG. 4. is a graph of the release of p-nitroaniline (PNA) from the matrix material comprised of poly p-carboxyphenoxyacetic anhydride [p(CPA)] over time, along with the percentage degradation of the matrix material itself [p(CPA)] over time.

FIGS. 3 and 4 demonstrate clearly that the release of p-nitroaniline follows the degradation of the polymer, indicative of an intact matrix with surface erosion. The obvious importance of this invention is that the polymer matrix does not remain to degrade slowly over time in vivo long after the drug has been delivered. This is the result of the fine uniform distribution of aliphatic and aromatic residues in the polymer.

Another useful property of this invention is that a polymer with a required degradation profile may be obtained by choosing the appropriate length of the aliphatic moiety. For example, p(CPV) with an aliphatic chain of four methylene groups degraded completely after two weeks while p(CPO) with seven methylene groups degraded about 120 days.

Figure 5:
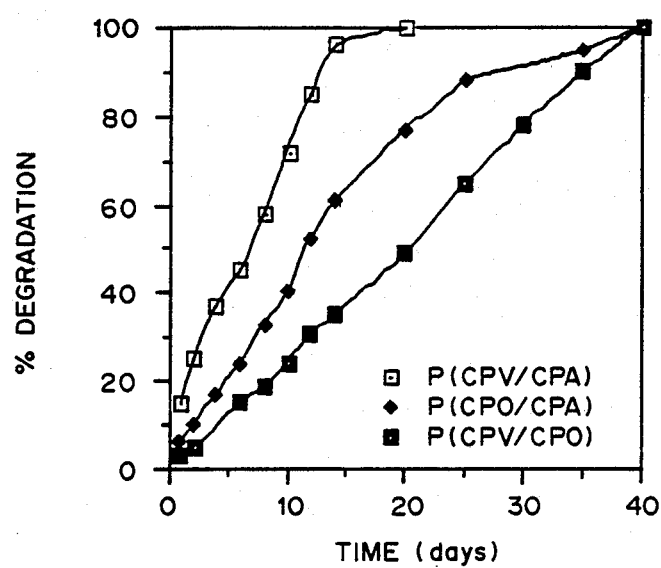
FIG. 5. is a graph of the degradation of copolymers p(CPV/CPA), p(CPO/CPA), and p(CPV/CPO) over time.

Copolymers of these aromatic-aliphatic monomeric diacids also display zero-order degradation, with a time frame indicative of the monomers selected. See FIG. 5.

This invention has been described with reference to its preferred embodiments. Variations and modifications of the method of synthesizing polymers with uniform aliphatic and aromatic residues and which display zero-order degradation profiles, and the polymers, will be obvious to those skilled in the art. It is intended that all of these variations and modifications be included within the scope of the appended claim.

We claim:

1. A polyanhydride having the general formula

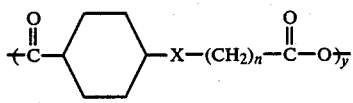

wherein X is selected from the group consisting of O and CH$_2$, n is an integer between 2 and 25, and y is at least 2, and wherein the polyanhydride is soluble in organic solvents and has a melting point of approximately 100° C. or less.

2. The polymer of claim 1 further comprising a bioactive compound for use in a controlled bioactive compound delivery device.

3. The polymers of claim 1 which have a melting point between 40° C. and 100° C.

4. The polymers of claim 1 which display zero order kinetic degradation profiles past 60% degradation.

5. The polymers of claim 1 formed by the polymerization of monomers selected from the group consisting of p-carboxyphenoxyvaleric acid, and p-carboxyphenoxyoctanoic acid.

6. The polymers of claim 5 further comprising a bioactive compound for use in a controlled drug delivery device.

7. The polymers of claim 5 which have a melting point between 40° C. and 100° C.

8. The polymers of claim 5 which display zero order kinetic degradation profiles past 60% degradation.

9. A method of preparing a controlled bioactive compound delivery device comprising
selecting monomers having both aromatic and aliphatic moieties which may be polymerized into a polyanhydride with a uniform distribution of aliphatic and aromatic residues in the polymer chain, having the general formula

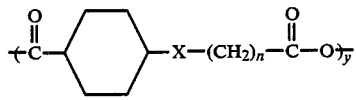

wherein X is selected from the group consisting of O and CH$_2$, n is an integer between 2 and 25, and y is at least 2, and
wherein the polyanhydride is soluble in organic solvents and has a melting point of approximately 100° C. or less.

10. The method of claim 15 further comprising polymerizing the monomers to form a polymer having the formula

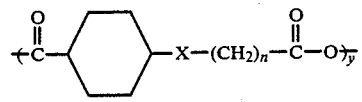

wherein X is selected from the group consisting of O and CH$_2$, n is an integer between 2 and 25, and y is at least 2.

11. The method of claim 10 further comprising:
providing a bioactive compound selected from the group consisting of proteins, drugs, saccharides, nucleic acid sequences, and combinations thereof.

12. The method of claim 9 further comprising polymerizing monomers selected from the group consisting of p-carboxyphenoxyalkanoic acids.

13. The method of claim 12 wherein the monomers are selected from the group consisting of p-carboxyphenoxyvaleric acid, and p-carboxyphenoxyoctanoic acid.

14. The method of claim 9 further comprising polymerizing the monomers to form a polymeric matrix, providing a bioactive compound, and embedding the bioactive compound in the polymeric matrix.

15. The method of claim 14 further comprising implanting the bioactive compound delivery device.

16. The method of claim 11 further comprising polymerizing the monomers with a bioactive compound.

17. The method of claim 16 further comprising implanting the controlled bioactive compound delivery device.

18. A polyanhydride with the general formula

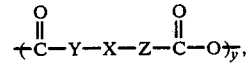

wherein X is selected from the group consisting of O and CH$_2$, Y is an aromatic, Z is an aliphatic having between 2 and 25 carbon molecules in the backbone, and y is at least 2, and
wherein the polyanhydride is soluble in organic solvents and has a melting point of approximately 1000° C. or less.

* * * * *